United States Patent
Davenport et al.

(10) Patent No.: US 8,283,930 B2
(45) Date of Patent: Oct. 9, 2012

(54) METHOD AND SYSTEM FOR COMPENSATING FOR VARIATION IN ATTENUATION MEASUREMENTS CAUSED BY CHANGES IN AMBIENT TEMPERATURE

(75) Inventors: David Michael Davenport, Niskayuna, NY (US); John Lofgren, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 412 days.

(21) Appl. No.: 12/569,258

(22) Filed: Sep. 29, 2009

(65) Prior Publication Data

US 2011/0074440 A1    Mar. 31, 2011

(51) Int. Cl.
*G01R 35/00* (2006.01)

(52) U.S. Cl. ........ 324/601; 343/703; 324/635; 324/639; 60/295

(58) Field of Classification Search .................. 324/601; 343/703
See application file for complete search history.

(56) References Cited

U.S. PATENT DOCUMENTS

| | | | | |
|---|---|---|---|---|
| 4,477,771 | A * | 10/1984 | Nagy et al. | 324/636 |
| 5,939,888 | A * | 8/1999 | Nelson | 324/640 |
| 6,249,129 | B1 * | 6/2001 | Burk et al. | 324/639 |
| 6,862,937 | B2 | 3/2005 | Fujita et al. | |
| 7,253,641 | B2 * | 8/2007 | Knitt et al. | 324/639 |
| 7,679,374 | B2 * | 3/2010 | Bromberg et al. | 324/637 |
| 2007/0024289 | A1 * | 2/2007 | Knitt et al. | 324/639 |
| 2007/0101705 | A1 * | 5/2007 | Knitt | 60/295 |
| 2007/0188372 | A1 * | 8/2007 | Leath | 342/26 R |
| 2008/0036649 | A1 * | 2/2008 | Lyon | 342/174 |
| 2008/0040014 | A1 * | 2/2008 | Yahata et al. | 701/99 |
| 2008/0297955 | A1 | 12/2008 | Ausserlechner | |
| 2011/0279334 | A1 * | 11/2011 | Smith et al. | 343/703 |

FOREIGN PATENT DOCUMENTS

| | | |
|---|---|---|
| GB | 1114157 A | 5/1968 |
| JP | 2008002349 A | 1/2008 |
| WO | 9202807 A1 | 2/1992 |
| WO | 9638721 A1 | 12/1996 |
| WO | 9853306 A1 | 11/1998 |

OTHER PUBLICATIONS

International Search Report and Written Opinion issued in connection with PCT/US2010/044637 Nov. 3, 2010.

* cited by examiner

*Primary Examiner* — Timothy J Dole
*Assistant Examiner* — Benjamin M Baldridge
(74) *Attorney, Agent, or Firm* — Global Patent Operation; Mark A. Conklin

(57) ABSTRACT

A method and apparatus for determining the attenuation of an RF signal caused by a DPF at an unknown or different ambient temperature than the temperature used for DPF sensor calibration is disclosed. The method and apparatus determine the sensor attenuation just prior to determining the DPF attenuation by disconnecting the antennas and determining the attenuation of a loopback path. This sensor attenuation can then be deducted from the attenuation determined for the normal path that includes the attenuation caused by the loopback path, the cables, and the DPF. This method compensates for variation in the attenuation of the sensor caused by changes in ambient temperature of the sensor. Further temperature compensation is be achieved by determining additional factors to account for variations caused by changes in ambient temperature.

6 Claims, 2 Drawing Sheets

METHOD AND SYSTEM FOR COMPENSATING FOR VARIATION IN ATTENUATION MEASUREMENTS CAUSED BY CHANGES IN AMBIENT TEMPERATURE

BACKGROUND OF THE INVENTION

The present invention relates to compensation for variation in attenuation measurements by a sensor caused by changes in the ambient temperature of the sensor.

In many sensor applications, it is necessary to determine the attenuation of a signal passing from a transmitter to a receiver. One such application is diesel particulate filter (DPF) sensors using radio frequency ("RF") signals across the DPF. A DPF is a device designed to trap and remove diesel particulate matter (i.e., soot) from the exhaust gas of diesel engines as the exhaust gas passes through the DPF. DPF can be used to reduce emissions and improve efficiency of internal combustion engines and after treatment systems. Since a DPF must periodically be cleaned when the soot loading of the DPF exceeds a certain threshold, DPF sensors can be employed to monitor the soot loading of a DPF. Different types of DPF sensors exist using different technologies to monitor the soot loading of a DPF, including RF technology. The DPF sensor can provide data relating to the amount of soot loading of the DPF to an engine control module (ECM), which can then determine when the DPF should be cleaned.

In a DPF sensor using RF signals, the power of an RF signal transmitted by an antenna located on one side of the DPF is compared to the power of that RF signal received by an antenna located on the other side of the DPF to measure the attenuation in the signal caused by the DPF. The DPF sensor or ECM can then correlate the attenuation caused by the DPF with the amount of soot loading of the DPF. For example, a particular attenuation value caused by the DPF coupled with other data (e.g., temperature across the DPF) indicates a particular amount of soot loading of the DPF.

A transfer function relating attenuation to soot loading for a particular type of DPF can be empirically determined over a range of frequencies at a particular exhaust gas temperature. For example, if an RF signal DPF sensor monitoring a DPF having inlet and outlet exhaust gas temperatures of 250° C. measures an attenuation value of 10 dB (i.e., 10 dB is lost across the DPF) for a 700 MHz signal, and an actual soot load (1.0 g/l) of the DPF is measured under those conditions (e.g., by weighing the DPF), the combination of the particular exhaust gas temperature (250° C.), attenuation value (10 dB), and frequency (700 MHz) is correlated to that measured soot load (1.0 g/l). Keeping the exhaust gas temperature constant, that process can be repeated over a range of soot loads and over a range of frequencies to correlate each attenuation value to a measured soot load at that particular temperature. Then, this same process can be repeated (i.e., measuring the actual soot load of the DPF at different soot loads at different frequencies) at several different exhaust gas temperatures.

Typically, this correlation process for an RF signal DPF sensor would take place in an environment where the ambient temperature of the sensor and its associated electronics is approximately room temperature (25° C.). However, since in the field, the RF signal DPF sensor can be exposed to a wide range of ambient temperatures (e.g., −40° C. to 85° C.), its performance (e.g., sensitivity of detectors, output power of the transmitter) will vary at these different ambient temperatures. For example, while at an ambient temperature of 25° C., an RF signal DPF sensor monitoring a DPF having an exhaust gas temperature of 250° C. measures an attenuation value of 10 dB for a 700 MHz signal for a soot load of 1.0 g/l, under the same exact filter conditions (exhaust gas temperature, filter soot load, and RF signal frequency) but with the sensor at a different ambient temperature, the sensor will measure a different attenuation value, which would then result in an incorrect correlation to soot load based on the correlation process performed at an ambient temperature of 25° C.

One solution to this problem is to perform the same correlation process that was performed at an ambient temperature of 25° C. at various temperatures over the wide range of possible ambient temperatures. However, such an effort would result in significant expenditures of time, resources, and money for each sensor that required correlation. Accordingly, it is desirable to be able to compensate for variation in attenuation measurements resulting from variations in the sensor performing the attenuation measurements caused by changes in ambient temperature without the need for additional measurements at temperatures other than 25° C.

BRIEF DESCRIPTION OF THE INVENTION

A method and apparatus for determining the attenuation of an RF signal caused by a DPF at an unknown or different ambient temperature than the temperature used for DPF sensor calibration is disclosed. The method and apparatus determine the sensor attenuation just prior to determining the DPF attenuation by disconnecting the antennas and determining the attenuation of a loopback path. This sensor attenuation can then be deducted from the attenuation determined for the normal path that includes the attenuation caused by the loopback path, the cables, and the DPF. This method compensates for variation in the attenuation of the sensor caused by changes in ambient temperature of the sensor. Further temperature compensation is be achieved by determining additional factors to account for variations caused by changes in ambient temperature.

BRIEF DESCRIPTION OF THE DRAWINGS

So that the manner in which the above recited features of the present invention can be understood in detail, a more particular description of the invention briefly summarized above, may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. The drawings are not necessarily to scale, emphasis generally being placed upon illustrating the principles of certain embodiments of invention.

Thus, for further understanding of the nature and objects of the invention, references can be made to the following detailed description, read in connection with the drawings in which.

DETAILED DESCRIPTION OF THE INVENTION

Figure 1:
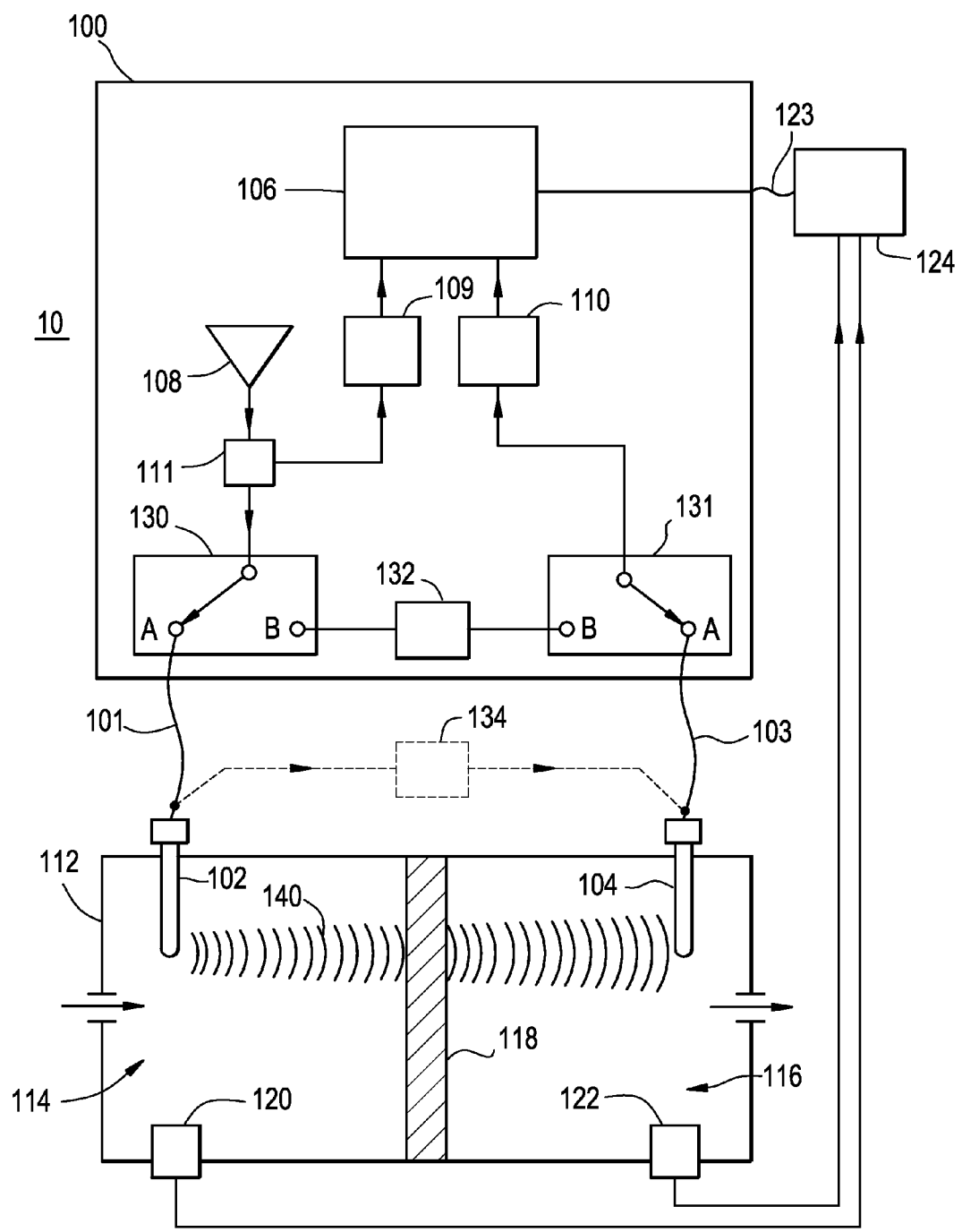
FIG. 1 illustrates a block diagram of a DPF system in one exemplary embodiment of the invention.

FIG. 1 illustrates a block diagram of a DPF system 10 in one exemplary embodiment of the invention. The DPF system 10 can comprise a DPF canister 112 containing the DPF 118 and a DPF sensor 100 for monitoring the DPF, with both the DPF canister 112 and the DPF sensor 100 communicating data to an ECM 124 to determine the soot loading of a DPF 118 using RF technology. Although this exemplary embodiment of the invention involves a DPF system 10 that determines the attenuation of an RF signal 140 to monitor the soot load of a DPF 118, it will be understood by persons of ordinary skill in the art that the invention can be used in a variety of other applications that determine the attenuation of a signal, including different DPF system 10 configurations.

The DPF canister 112 has an inlet side 114 through which exhaust gas passes before passing through the DPF 118 and an outlet side 116 through which exhaust gas passes after passing through the DPF 118. The DPF 118 can be constructed of materials that are selected for their compatibility with diesel exhaust, and diesel exhaust particulates generated by diesel engines. The DPF canister 112 can also comprise an inlet temperature sensor 120 for measuring the temperature of the inlet side 114 and an outlet temperature sensor 122 for measuring the temperature of the outlet side 116. The temperatures of the inlet side 114 and the outlet side 116 can be communicated to the ECM 124.

In order to determine the soot loading of a DPF 118 using RF technology, a transmit antenna 102 can be positioned on the inlet side 114 of the DPF 118 and a receive antenna 104 positioned on the outlet side 116 of the DPF 118. The DPF system 10 can be configured so that the RF signal 140 transmitted by the transmit antenna 102 is transmitted through and attenuated by the soot in the DPF 118 before being received by the receive antenna 104. The RF signal 140 can transmit at one or more frequencies that are attenuated by soot in the DPF 118 (e.g., the range of 700 MHz to about 900 MHz). The measured attenuation of the RF signal 140 across the DPF 118 at each of these frequencies along with the exhaust gas temperature can then be used to determine the amount of soot loading of the DPF 118 (e.g., the greater the attenuation, the greater the soot loading).

A DPF sensor 100 can comprise a transmitter 108 that generates the RF signal 140 at one or more frequencies (e.g., the range of 700 MHz to about 900 MHz) that is conducted to the transmit antenna 102. In order to determine the attenuation of the RF signal 140 caused by the DPF 118, the DPF sensor 100 can comprise a directional coupler 111 and a transmit detector 109 for measuring the power (dBm) of the RF signal 140 before passing through the DPF 118 and a receive detector 110 for measuring the power (dBm) of the RF signal 140 after passing through the DPF 118. The detectors 109, 110 can be, e.g., RF logarithmic detectors that can detect the power level (dBm) of the RF signal 140 and provide a corresponding output voltage level (Volts DC). Examples of such RF power detectors are the AD8312 from Analog Devices and the LT5537 from Linear Technology. The detectors 109, 110 can provide these power measurements to the DPF sensor controller 106, which can communicate the power measurements or related data (e.g., attenuation caused by the DPF 118) via an interface cable 123 to, e.g., a computer, a laptop, and/or ECM 124.

In the embodiment illustrated in FIG. 1, the transmit detector 109 is located proximate the transmitter 108 and measures the power of the RF signal 140 at a particular frequency before it passes through, and is attenuated by, internal components (e.g., electronics, circuitry, etc.) of the DPF sensor 100, including a transmit switch 130, and a transmit cable 101 before reaching the transmit antenna 102. Similarly, the receive detector 110 measures the power of the RF signal 140 received by the receive antenna 104 after it passes through, and is attenuated by, a receive cable 103 and internal components of the DPF sensor 100, including a receive switch 131.

Since the difference in power (dB) between the power of the RF signal 140 at a particular frequency measured by the transmit detector 109 and the receive detector 110 includes the attenuation caused by the DPF 118 as well as the attenuation caused by the transmit cable 101, receive cable 103, and internal components of the DPF sensor 100 (e.g., transmit switch 130 and receive switch 131), in order to determine just the attenuation caused by the DPF 118, it is necessary to determine and subtract the amount of attenuation caused by the other sources of attenuation (i.e., cables 101, 103, DPF sensor 100 components, etc.) from the total attenuation measured by the detectors 109, 110 as shown in exemplary equation 1:

$$A_{DPF}(i) = A_{TN}(i) - A_C(i) - A_{SLB}(i) \tag{1}$$

where, i = frequency of the RF signal 140;

$A_{DPF}(i)$ = attenuation (dB) caused by the DPF 118 at frequency i;

$A_{TN}(i)$ = total attenuation (dB) measured by the detectors 109, 110 at frequency i in normal mode (described below);

$A_C(i)$ = attenuation (dB) caused by the cables 101, 103 at frequency i in calibration mode (described below); and $A_{SLB}(i)$ = attenuation (dB) caused by the internal components of the DPF sensor 100 at frequency i in loopback mode (described below).

From equation 1, it can be seen that in order determine attenuation of an RF signal 140 at a particular frequency caused by the DPF 118 using a DPF sensor 100, the sensor 100 can be calibrated to determine the actual sensor attenuation ($A_{SLB}(i)$) and the actual cable attenuation ($A_C(i)$) over a range of frequencies.

Referring again to FIG. 1, in order to calibrate the DPF sensor 100 at room temperature (25° C.) to determine the attenuation caused by the internal components of the DPF sensor 100, the transmit switch 130 and the receive switch 131 can be set to position "B" to place the DPF sensor 100 in loopback mode. In loopback mode, the cables 101, 103 and antennas 102, 104 are disconnected from the DPF sensor 100, forming a loopback path between RF transmitter 108 and the receive detector 110 that only includes the internal components of the DPF sensor 100. In one embodiment, the loopback path can also include a frequency-independent loopback mode attenuator 132 (e.g., a 10 dB resistor attenuator) ($A_{ALB}$=10 dB).

Once configured in loopback mode, the transmitter 108 can sweep through the frequency range from 700 MHz to 900 MHz in 1 MHz steps for a total of 201 steps/sweeps. For each of those steps (i=700 MHz, 701 MHz, ... 900 MHz), the transmitted power (dBm) ($P_{TLB}(i)$) can be measured by the transmit detector 109, while the received power (dBm) ($P_{RLB}(i)$) can be measured by the receive detector 110. It is assumed for the purposes of simplifying the description of this exemplary embodiment that there is no reflected power from a mismatched load or the transmit antenna 102, and that therefore the power measured by the transmit detector 109 ($P_T(i)$) is the power generated by the transmitter 108. In order to take into account any reflected power, an additional detector (not shown) could be used in the DPF sensor 100 to determine the power that was actually transmitted to the transmit antenna 102 by subtracting the reflected power from the power measured by the transmit detector 109 ($P_T(i)$).

The measured powers for transmitted power (dBm) ($P_{TLB}(i)$) and received power (dBm) ($P_{RLB}(i)$) for each of the frequencies (i) can then be provided to the DPF sensor controller 106, which can then determine the corresponding loopback mode sensor attenuation ($A_{SLB}(i)$) at each of those frequencies using exemplary equation 2:

$$A_{SLB}(i) = P_{TLB}(i) - P_{RLB}(i) - A_{ALB} \quad (2)$$

where,
- i=frequency of the RF signal 140;
- $A_{SLB}(i)$=attenuation (dB) caused by the internal components of the DPF sensor 100 at frequency i in loopback mode;
- $P_{TLB}(i)$=transmitted power (dBm) measured by the transmit detector 109 at frequency i in loopback mode;
- $P_{RLB}(i)$=received power (dBm) ($P_R(i)$) measured by the receive detector 110 at frequency i in loopback mode; and
- $A_{ALB}$=attenuation (dB) of the loopback mode attenuator 132.

For example, for an RF signal 140 transmitted at a frequency of 700 MHz (i=0) with the DPF sensor 100 in loopback mode at an ambient temperature of 25° C., if the measured transmitted power ($P_{TLB}(0)$) was 1.6 dBm, the measured received power ($P_{RLB}(0)$) was −13.2 dBm, and the loopback mode attenuator 132 had an attenuation of 10 dB ($A_{ALB}$=10 dB), the loopback mode sensor attenuation ($A_{SLB}(0)$) would be 4.8 dB.

Referring again to FIG. 1, in order to calibrate the DPF sensor 100 at room temperature (25° C.) to determine the attenuation caused by the cables 101, 103, the transmit switch 130 and the receive switch 131 can be set to position "A." In addition, the antennas 102, 104 are disconnected from the cables 101, 103 and a frequency-independent calibration mode attenuator 134 (e.g., a 10 dB resistor attenuator) having the same attenuation value as the loopback mode attenuator 132 is connected between the cables 101, 103. This configuration (i.e., switches 130, 131 set to position "A" with the calibration mode attenuator 134 connected) places the DPF sensor 100 in calibration mode. As can be seen in FIG. 1, given that the calibration mode attenuator ($A_{AC}$=10 dB) is the same as the loopback mode attenuator ($A_{ALB}$=10 dB), any difference in attenuation introduced in the normal path from that of the loopback path would be attributable to the cables 101, 103.

Once configured in calibration mode, the transmitter 108 can sweep through the frequency range from 700 MHz to 900 MHz in 1 MHz steps for a total of 201 steps/sweeps. For each of those steps (i=700 MHz, 701 MHz, . . . 900 MHz), the transmitted power (dBm) ($P_{TC}(i)$) can be measured by the transmit detector 109, while the received power (dBm) ($P_{RC}(i)$) can be measured by the receive detector 110. These measured powers for each of the frequencies (i) can then be provided to the DPF sensor controller 106, which can then determine the corresponding cable attenuation ($A_C(i)$) at each of those frequencies using exemplary equation 3:

$$A_C(i) = P_{TC}(i) - P_{RC}(i) - A_{AC} - A_{SLB}(i) \quad (3)$$

where,
- i=frequency of the RF signal 140;
- $A_C(i)$=attenuation (dB) caused by the cables 101, 102 at frequency i in calibration mode;
- $P_{TC}(i)$=transmitted power (dBm) measured by the transmit detector 109 at frequency i in calibration mode;
- $P_{RC}(i)$=received power (dBm) ($P_R(i)$) measured by the receive detector 110 at frequency i in calibration mode;
- $A_{AC}$=attenuation (dB) of the calibration mode attenuator 134; and
- $A_{SLB}(i)$=attenuation (dB) caused by the internal components of the DPF sensor 100 at frequency i determined in loopback mode.

For example, for an RF signal 140 transmitted at a frequency of 700 MHz (i=0) with the DPF sensor 100 in calibration mode at an ambient temperature of 25°, if the measured transmitted power ($P_{TC}(0)$) was 1.6 dBm, the measured received power ($P_{RC}(0)$) was −15.8 dBm, the calibration mode attenuator 134 had an attenuation of 10 dB ($A_{AC}$=10 dB), and the loopback mode sensor attenuation ($A_{SLB}(0)$) was determined to be 4.8 dB (as discussed above), the calibration mode cable attenuation ($A_C(0)$) would be 2.6 dB. Given that the loopback mode attenuator 132 and the calibration mode attenuator 134 have the same attenuation value in this example ($A_{ALB}$=$A_{AC}$=10 dB), equations 2 and 3 can be modified to not expressly subtract the attenuator 132, 134 values since those values would effectively cancel each other out when the sensor attenuation ($A_{SLB}(i)$) is subtracted from the difference between the transmitted power and the received power ($P_{TC}(i)$−$P_R(i)$) in calibration mode.

Combining the attenuation caused by the cables ($A_C(0)$=2.6 dB) with the attenuation caused by the internal components of the DPF sensor 100 ($A_{SLB}(i)$=4.8 dB), for an RF signal 140 transmitted at a frequency of 700 MHz (i=0) at an ambient temperature of 25° C., a total of 7.4 dB of attenuation would be caused by the internal components of the DPF sensor 100 and the cables 101, 103.

Referring again to equation 1 above, if the DPF sensor 100 were configured in normal mode (i.e., switches 130, 131 were set to position "A" and the antennas 102, 104 were connected to cables 101, 103 instead of the calibration mode attenuator 134), for an RF signal 140 transmitted at a frequency of 700 MHz (i=0) at an ambient temperature of 25° C., the attenuation ($A_{DPF}(0)$) caused by the DPF 118, would be the total attenuation value ($A_{TN}(0)$) measured by the detectors 109, 110 minus 7.4 dB (i.e., the attenuation caused by the cables and the sensor at that frequency): $A_{DPF}(0) = A_{TN}(0) - 4.8 - 2.6$ If the DPF sensor 100 was only used in an ambient temperature that was the same as the ambient temperature used for the calibration to determine the sensor attenuation ($A_{SLB}(i)$), the above described calibration process might be sufficient (i.e., the actual sensor attenuation ($A_{SLB}(0)$) should always be 4.8 dB). However, since in the field, the DPF sensor 100 can be exposed to a wide range of ambient temperatures (e.g., −40° C. to 85° C.) and the sensor attenuation can vary based on temperature, the actual sensor attenuation at these different temperatures will vary (i.e., the actual sensor attenuation ($A_{SLB}(0)$) will not always be 4.8 dB). One solution to this problem is to perform the same calibration process that was performed at an ambient temperature of 25° C. at various temperatures over the wide range of possible ambient temperatures and store the various sensor attenuations for the various temperatures and frequencies. However, such an effort would result in significant expenditures of time, resources, and money for each DPF sensor 100.

Instead, in one embodiment of the invention, just prior to conducting each and every sweep periodically determining the DPF 118 attenuation ($A_{DPF}(i)$) at an unknown or different ambient temperature than the temperature used for calibration (i.e., 25° C.), the DPF sensor 100 can first be configured in loopback mode as discussed above (i.e., switches 130, 131 set to position "B" with loopback mode attenuator 132). Once configured in loopback mode, the transmitter 108 can sweep through the frequency range from 700 MHz to 900 MHz in 1 MHz steps for a total of 201 steps/sweeps and measure the transmitted power (dBm) ($P_{TLB}(i)$) and received power (dBm) ($P_{RLB}(i)$) for each of the frequencies (i) and provide those measurements to the DPF sensor controller 106, which can then determine the corresponding loopback mode sensor attenuation ($A_{SLB}(i)$) at each of those frequencies using equation 2. By doing so, an accurate sensor attenuation ($A_{SLB}(i)$) is provided immediately before determining the DPF 118 attenuation ($A_{DPF}(i)$) at an unknown or different ambient temperature.

Next, if the same cable attenuation ($A_C(i)$) determined during calibration (or a modified cable attenuation based on a change in ambient temperature) is used, based on equation 1, all that remains in order to determine the DPF 118 attenuation ($A_{DPF}(i)$) is to measure the total attenuation $A_{TN}(i)$ in normal mode.

After the DPF sensor 100 is configured in normal mode (i.e., switches 130, 131 set to position "A" and the antennas 102, 104 connected to cables 101, 103), the transmitter 108 can sweep through the frequency range from 700 MHz to 900 MHz in 1 MHz steps for a total of 201 steps/sweeps and measure the transmitted power (dBm) ($P_{TN}(i)$) and received power (dBm) ($P_{RN}(i)$) for each of the frequencies (i) and provide those measurements to the DPF sensor controller 106, which can then determine the corresponding normal mode total attenuation ($A_{TN}(i)$) at each of those frequencies using exemplary equation 4:

$$A_{TN}(i)=P_{TN}(i)-P_{RN}(i) \qquad (4)$$

where,
- i=frequency of the RF signal 140;
- $A_{TN}(i)$=total attenuation (dB) measured by the detectors 109, 110 at frequency i in normal mode;
- $P_{TN}(i)$=transmitted power (dBm) measured by the transmit detector 109 at frequency i in normal mode; and
- $P_{RN}(i)$=received power (dBm) measured by the receive detector 110 at frequency i in normal mode.

Once the normal mode total attenuation is known ($A_{TN}(i)$) at the unknown or different ambient temperature, the DPF sensor controller 106 can then determine the attenuation caused by the DPF 118 ($A_{DPF}(i)$) using equation 1 by subtracting the sensor attenuation ($A_{SLB}(i)$) determined in loopback mode at that same unknown or different ambient temperature and subtracting the cable attenuation ($A_C(i)$).

For example, for an RF signal 140 transmitted at a frequency of 700 MHz (i=0) with the DPF sensor 100 at an unknown or different ambient temperature, if the normal mode total attenuation ($A_{TN}(0)$) was 28.0 dB, the loopback mode sensor attenuation ($A_{SLB}(0)$) was 5.0 dB (i.e., different than the attenuation value of 4.8 dB determined at an ambient temperature of 25° C.), and the cable attenuation ($A_C(0)$) was 2.6 dB, the attenuation caused by the DPF 118 ($A_{DPF}(0)$) would be 20.4 dB.

In order to determine the accuracy of this compensation, a significant amount of empirical data can be acquired. Depending on the particular electronics used in the DPF sensor 100 (e.g., detectors 109, 110), the empirical data may demonstrate that the compensation for variation in attenuation measurements of the DPF sensor 100 caused by ambient temperature variation by determining the loopback mode sensor attenuation ($A_{SLB}(i)$) before each DPF 118 attenuation measurement is sufficient to achieve the required accuracy for a particular application. In other cases, the empirical data may demonstrate a need for further compensation.

For example, certain RF logarithmic detectors, which detect the power level of the RF signal 140 and provide a corresponding output voltage level (Volts DC), exhibit an amplitude dependent error over temperature. For one RF logarithmic detector, there can be a much wider variation in readings over temperature at low signal levels (e.g., −30 dBm and lower) than there is at high signal levels (e.g., −10 dBm and higher). Accordingly, in some cases, it may be necessary to apply a scaling factor to the value determined above to be the attenuation caused by the DPF 118 ($A_{DPF}(i)$) to further compensate for temperature variation based on the empirical data.

In one embodiment, the empirical data that may be used to determine what further compensation is required can be acquired using the following process: At one or more particular ambient temperature(s) (e.g., −40° C., −20° C., 0° C., 20° C., 25° C., 40° C., 65° C., and 85° C.), the DPF system 10 of FIG. 1 can be configured in loopback mode (switches 130, 131 set to position "B" with or without the loopback mode attenuator 132) and the transmitter 108 can sweep through the frequency range from 700 MHz to 900 MHz in 1 MHz steps for a total of 201 steps/sweeps measuring and recording the transmitted power ($P_{TLB}(i)$) and the received power (dBm) ($P_{RLB}(i)$. At that same ambient temperature, the DPF system 10 of FIG. 1 can be configured in calibration mode (i.e., switches 130, 131 set to position "A" with the calibration mode attenuator 134 connected) and the transmitter 108 can sweep through the frequency range from 700 MHz to 900 MHz in 1 MHz steps for a total of 201 steps/sweeps measuring and recording the transmitted power ($P_{CC}(i)$) and the received power (dBm) ($P_{CC}(i)$) at different attenuation values for the calibration mode attenuator 134 (e.g., $A_{AC}$=0 dB, 10 dB, 20 dB, 30 dB, 40 dB, 50 dB, and 60 dB). Once all of the sweeps have been completed, the same process can be repeated at the next ambient temperature.

In addition to this empirical data, data acquired during the calibration and normal operation of the sensor can also be used to further compensate for temperature variation. For example, during calibration in loopback mode at an ambient temperature of 25° C., the transmitter 108 can sweep through the frequency range from 700 MHz to 900 MHz in 1 MHz steps for a total of 201 steps. For each of those steps (i=700 MHz, 701 MHz, . . . 900 MHz), the transmitted power (dBm) ($P_{TLBCAL}(i)$) for each frequency can be measured and provided to the DPF sensor controller 106, which can permanently store those values. These transmitted power ($P_{TLBCAL}(i)$) values can be used to provide a normalized condition for the DPF sensor 100 to account for changes in detector 109, 110 performance (e.g., detector output based on a certain input) with temperature.

Similarly, during operation, in loopback mode at an unknown or different ambient temperature just prior to determining DPF 118 attenuation, the transmitter 108 can periodically sweep through the frequency range from 700 MHz to 900 MHz in 1 MHz steps for a total of 201 steps/sweeps. For each of those steps (i=700 MHz, 701 MHz, . . . 900 MHz), the transmitted power (dBm) ($P_{TLBPER}(i)$) for each frequency can be measured and provided to the DPF sensor controller 106, which can permanently store those values. These periodically determined transmitted power ($P_{TLBPER}(i)$) values can be used to compare to the calibrated transmitted power ($P_{TLBCAL}(i)$) values to compensate for temperature dependent changes in the detectors 109, 110.

The transmitted power values ($P_{TLBCAL}(i)$ and $P_{TLBPER}(i)$) can be used to form a temperature compensation factor (TCOMP(i)) as shown in exemplary equation 5:

$$TCOMP(i)=P_{TLBCAL}(i)-P_{TLBPER}(i) \qquad (5)$$

where,
- i=frequency of the RF signal 140;
- TCOMP(i)=temperature compensation factor;
- $P_{TLBCAL}(i)$=transmitted power (dBm) measured by the transmit detector 109 at frequency i in loopback mode (during factor calibration); and
- $P_{TLBPER}(i)$=transmitted power (dBm) measured by the transmit detector 109 at frequency i in normal mode (periodic measurements); and For example, for an RF signal 140 transmitted at a frequency of 700 MHz (i=0) with the DPF sensor 100 in loopback mode at an ambient temperature of 25° C., the measured transmitted power ($P_{TLBCAL}(0)$) was 1.6 dBm. However, for an RF signal 140 transmitted at a frequency of 700 MHz (i=0)

with the DPF sensor 100 in loopback mode at an ambient temperature of 85° C., the measured transmitted power ($P_{TLBPER}(0)$) was 2.4 dBm. Under these conditions, the temperature compensation factor (TCOMP(i)) would be −0.8 dB.

A review of the empirical data acquired during the procedure described above determined that the temperature compensation factor (TCOMP(i)) can be used in conjunction with a coefficient (AMP(i)) that is based on the amplitude of the initially determined DPF 118 attenuation ($A_{DPF}(i)$). Based on the empirical data, this amplitude coefficient (AMP(i)) can be expressed using a polynomial as shown in exemplary equation 6:

$$AMP(i) = aX + bX^2 + cX^3 + d \quad (6)$$

where,
i=frequency of the RF signal 140;
AMP(i)=amplitude coefficient;
$X = A_{DPF}(i)$=initially determined attenuation (dB) caused by the DPF 118 at frequency i;
a=−4.6409E-02;
b=5.1136E-04;
c=1.6970E-05; and
d=7.8825E-03.

Figure 2:
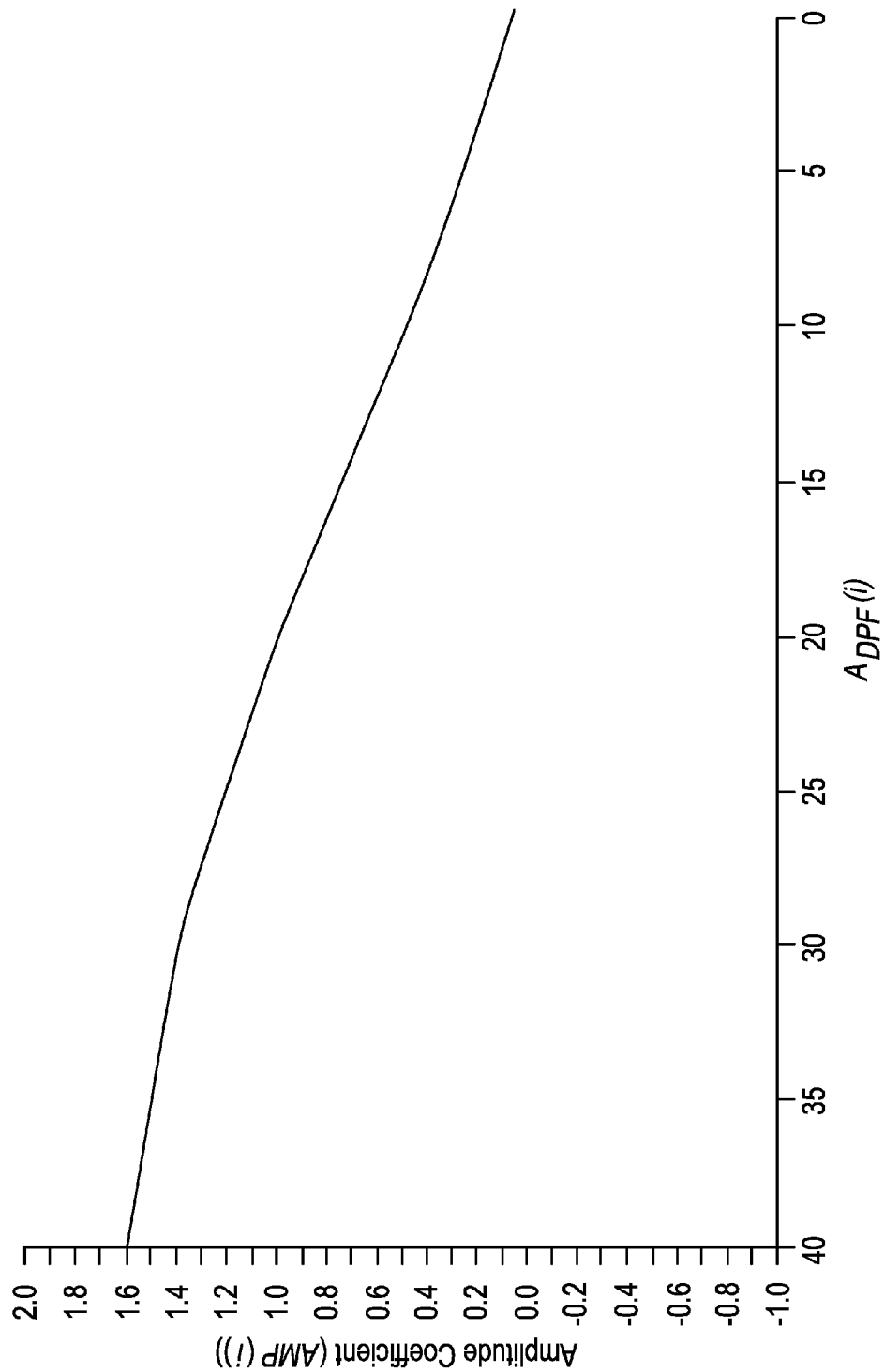
FIG. 2 is a plot of an amplitude coefficient versus initially determined attenuation (dB) caused by the DPF at a particular frequency.

FIG. 2 shows a plot of the amplitude coefficient (AMP(i)) versus the initially determined attenuation (dB) caused by the DPF 118 at a particular frequency ($A_{DPF}(i)$). The data shows that the amplitude coefficient (AMP(i)) is much greater when the initially determined attenuation (dB) caused by the DPF 118 ($A_{DPF}(i)$) is relatively high (e.g., 40 dB).

As discussed above, the temperature compensation factor (TCOMP(i)) can be used in conjunction with the amplitude coefficient (AMP(i)) to determine a compensated DPF 118 attenuation ($A_{DPFC}(i)$) using exemplary equation 7:

$$A_{DPFC}(i) = A_{DPF}(i) + AMP(i) * TCOMP(i) \quad (7)$$

where,
i=frequency of the RF signal 140;
$A_{DPFC}(i)$=compensated attenuation (dB) caused by the DPF 118 at frequency i;
$A_{DPF}(i)$=initially determined attenuation (dB) caused by the DPF 118 at frequency i;
AMP(i)=amplitude coefficient; and
TCOMP(i)=temperature compensation factor.

For example, for an RF signal 140 transmitted at a frequency of 700 MHz (i=0) with the DPF sensor 100 in normal mode at an ambient temperature of 85° C., the initially determined attenuation (dB) caused by the DPF 118 ($A_{DPF}(i)$) was 21.0 dB, which yields a amplitude coefficient (AMP(i)) at that frequency of 1.05. Using the temperature compensation factor (−0.8 dB) determined above for an RF signal 140 transmitted at a frequency of 700 MHz (i=0) with the DPF sensor 100 in loopback mode at an ambient temperature of 85° C., the compensated attenuation (dB) caused by the DPF 118 ($A_{DPFC}(i)$) would be 20.1, a correction of 0.9 dB.

The DPF sensor controller 106 can communicate the DPF 118 attenuation values for all of the frequencies as well as the mean and standard deviation for those values to the ECM 124. The ECM can then use these DPF 118 attenuation values along with other data (e.g., exhaust gas temperature) to determine the soot load of the DPF 118.

This written description uses examples to disclose the invention, including the best mode, and also to enable any person skilled in the art to make and use the invention. For example, many different equations could be used to determine the various attenuation values without departing from the spirit and scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for determining the attenuation of a radio frequency (RF) signal caused by a diesel particulate filter (DPF) using a system comprising an RF transmitter for generating said RF signal connected to a transmit antenna positioned on a first side of said DPF via a transmit cable, a transmit detector and receive detector for measuring the power of said RF signal before and after passing through said DPF, and a receive antenna positioned on a second side of said DPF connected to said receive detector via a receive cable, the method comprising the steps of:
   (a) disconnecting said transmit cable and said transmit antenna from said RF transmitter;
   (b) disconnecting said receive cable and said receive antenna from said receive detector;
   (c) forming a first path between said RF transmitter and said receive detector that does not include said transmit cable, said transmit antenna, said receive cable, and said receive antenna;
   (d) generating said RF signal at a first frequency;
   (e) determining the attenuation of said RF signal caused by said first path at said first frequency at a first ambient temperature based on the difference between the power of said RF signal before traveling through said first path and the power of said RF signal after traveling through said first path;
   (f) connecting said transmit antenna to said RF transmitter via said transmit cable;
   (g) connecting said receive antenna to said receive detector via said receive cable;
   (h) forming a second path between said RF transmitter and said receive detector that does include said transmit cable, said transmit antenna, said receive cable, and said receive antenna;
   (i) determining the attenuation of said RF signal caused by said second path at said first frequency at said first ambient temperature based on the difference between the power of said RF signal before traveling through said second path and the power of said RF signal after traveling through said second path; and
   (j) determining the attenuation of said RF signal caused by said DPF at said first frequency at said first ambient temperature by subtracting from said attenuation caused by said second path the attenuation caused by sources in said first path that are also present in said second path and the attenuation caused by said transmit cable and said receive cable.

2. The method of claim 1, further comprising the step of repeating steps (a) through (j) for a plurality of frequencies of said RF signal at said first ambient temperature.

3. The method of claim 1, further comprising the steps of: measuring the power of said RF signal at said first frequency at a calibration ambient temperature before traveling through said first path;
   measuring the power of said RF signal at said first frequency at said first ambient temperature before traveling through said first path;
   determining a temperature compensation factor based on the difference between said power of said RF signal at said first frequency at said calibration temperature and said power of said RF signal at said first frequency at said first ambient temperature;
   determining an amplitude scaling factor to compensate for variations in said power measurements of said receive detector based on changes in ambient temperature at said first frequency; and determining a compensated attenuation of said RF signal caused by said DPF at said first frequency at said first ambient temperature based on said temperature compensation factor and said amplitude scaling factor.

4. The method of claim 3, wherein said amplitude scaling factor is based on empirical data acquired from operating said system at different ambient temperatures and different DPF attenuation values.

5. A system for determining the attenuation of an RF signal caused by a diesel particulate filter (DPF) comprising:
 an RF transmitter for generating said RF signal;
 a transmit detector for measuring the power of said RF signal before passing through said DPF;
 a receive detector for measuring the power of said RF signal after passing through said DPF;
 a transmit antenna positioned on a first side of said DPF;
 a receive antenna positioned on a second side of said DPF;
 a transmit switch connected to said RF transmitter having a first position wherein said RF signal is transmitted to said transmit antenna via a transmit cable and a second position wherein said RF signal is transmitted to a receive switch;
 said receive switch connected to said receive detector having a first position wherein said RF signal is received from said receive antenna via a receive cable and a second position wherein said RF signal is received from said transmit switch; and
 a path for transmitting said RF signal from said transmit switch to said receive switch when both switches are in said second positions, said path comprising an attenuator with an attenuation that is substantially independent of frequency in an RF frequency band of interest.

6. The system of claim 5, further comprising a controller for receiving said power measurements from said transmit detector and said receive detector and calculating attenuation considering ambient temperature.

* * * * *